United States Patent [19]

Shalaby et al.

[11] 4,433,161

[45] Feb. 21, 1984

[54] METHYL P-(ω-ACETOXYALKOXY) BENZOATE AND METHOD OF PREPARATION

[75] Inventors: Shalaby W. Shalaby, Mountainville; Edgar S. Schipper, Cranford; Donald F. Koelmel, Lebanon, all of N.J.

[73] Assignee: Ethicon, Inc., Somerville, N.J.

[21] Appl. No.: 355,976

[22] Filed: Mar. 8, 1982

[51] Int. Cl.$^3$ .............................................. C07C 69/78
[52] U.S. Cl. ........................................ 560/66; 560/64
[58] Field of Search ..................................... 560/64, 66

[56] References Cited

U.S. PATENT DOCUMENTS 4,016,186  4/1977  Kondo et al. .................... 560/64

*Primary Examiner*—Paul J. Killos
*Attorney, Agent, or Firm*—Nancy A. Bird; Charles J. Metz

[57] ABSTRACT

A novel family of diesters, methyl p-(ω-acetoxyalkoxy) benzoate wherein the alkoxy group has a chain length of 2 to 6, the method of preparation of the diesters, polymerization of the diesters and their use to form methyl p-(ω-hydroxy-n-alkoxy) benzoate.

5 Claims, No Drawings

METHYL P-(ω-ACETOXYALKOXY) BENZOATE AND METHOD OF PREPARATION

BACKGROUND OF THE INVENTION

Flexible copolymers of p-(hydroxyalkoxy) benzoic acid or its methyl ester are disclosed in U.S. Ser. No. 253,418. As set forth in the "Background of the Invention" in that application, p-(hydroxyalkoxy) benzoic acids had been used in fibers and films which exhibited good strength, but their copolymerization with flexible chain components to produce flexible copolyesters had not been suggested. The present invention comprises a novel diester and method of making the same which diester may be used to produce the p-(hydroxyalkoxy) benzoic acids or their methyl esters of the prior application or to produce the flexible copolyesters of the prior application directly from the diester, without the intermediate step of producing the p-(hydroxyalkoxy) benzoic acid or its methyl ester. The use of the diester produces greater yields and enhanced purity of the p-(hydroxyalkoxy) benzoic acid or its methyl ester.

SUMMARY OF THE INVENTION

The present invention comprises a novel family of diesters, methyl p-(ω-acetoxyalkoxy) benzoate having the following structural formula:

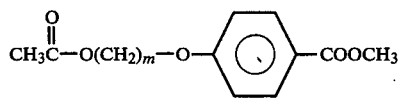

where m=2 to 6. The novel method of producing the diester comprises O-alkylation of methyl(p-hydroxy) benzoate using a α,ω acetoxyhaloalkane in the presence of an organic solvent and a suitable base under substantially anhydrous conditions.

The invention also comprises the novel process for producing methyl p-(ω-hydroxy-n-alkoxy) benzoate by the acid catalyst alcoholysis of the diester. The invention also comprises the method of self-condensation of the diester, and of producing copolyesters from the diester monomers.

DESCRIPTION OF THE INVENTION

The novel diesters of the present invention may be produced by the O-alkylation of methyl (p-hydroxy) benzoate using an α,ω acetoxy bromo- or chloro-n-alkane, in the presence of a suitable base and an organic solvent, under substantially anhydrous conditions. A typical reaction scheme is set out below:

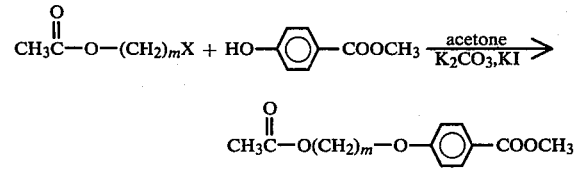

where X=Br, Cl and m=2–6, and preferably is 4. Another suitable base, for use alone or in conjunction with potassium iodide, is sodium carbonate. The following are examples for the preparation of diester.

Example 1: Methyl p-(4-acetoxybutoxy) benzoate

Into a 2 l. 3-necked flask fitted with a stirrer and reflux condenser and topped by a drying tube were placed 152 g (1.0 M) of methyl p-hydroxybenzoate, 197 g (1.01 M) of 4-bromobutyl acetate, 20 g (0.12 M) potassium iodide and 750 ml of dry acetone. To this was added 140 g (1.0 M) of anhydrous potassium carbonate powder. The mixture was refluxed while stirring for 48 hours. The mixture was filtered, the precipitate was washed with 100 ml of acetone and the filtrates were combined and evaporated to dryness. The solid residue was triturated with 1 l. of water, the mixture was filtered and the solid was washed thoroughly with water until the pH of the filtrate was neutral. The product was dried overnight in a nitrogen filled circulating forced gas oven. The dried product was washed well with 2 l. of either petroleum ether or hexane. After another drying cycle there remained 243.9 g (91.6%) of product, m.p. 49°–51° C.

Material of highest purity could be obtained by recrystallization in absolute ether or toluene, giving a yield of 193.7 g (72.7% overall yield corresponding to 79% recovery upon recrystallization) of melting point 52°–54° C.

A repetition of the procedure on a 15 M scale in which granular instead of powdered anhydrous potassium carbonate was employed gave a 95.7% yield of product, m.p. 54° C.

Example 2: Methyl p-(2-acetoxyethoxy) benzoate

Methyl p-hydroxy benzoate (15.2 g, 0.1 moles), 2-bromoethylacetate (16.7 g, 0.1 moles, b.p.=158°–159° C., $\eta_D^{23}=1.4548$), anhydrous $K_2CO_3$ (13.8 g, 0.1 moles), and anhydrous KI (1.7 g, 0.01 moles) were refluxed in 76 ml of acetone, with thorough mixing, for 68 hours. After filtration of the reaction mixture, the liquid portion of the reaction mixture was placed on a rotary evaporator and the acetone was distilled off at room temperature. Acetone evaporation produced an oil, which crystallized upon standing at room temperature. This solid was then extracted with 75 ml of diethyl ether. Ether evaporation yielded 11 g of solid product. Two recrystallizations of this solid from toluene produced a sample which melted from 76° to 78° C.

The novel diesters may be used to form the corresponding methyl p-(ω-hydroxyalkoxy) benzoates which may be used to form flexible copolyesters as set forth in U.S. Ser. No. 253,418. The acid catalyzed alcoholysis of the diesters can be used to yield the corresponding monomeric hydroxyesters according to the following scheme:

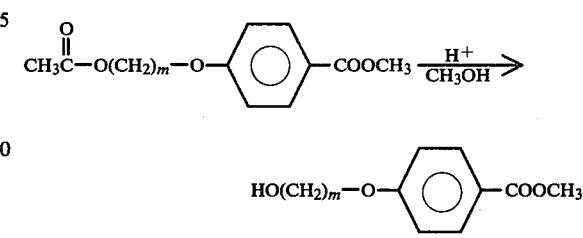

where H+ is an inorganic (e.g. $H_2SO_4$) or an organic acid and m=2–6. Examples of suitable organic acid catalysts are p-toluene sulfonic acid and sulfonated polystyrene. An example of the preparation of methyl p-(ω-hydroxyalkoxy) benzoate from the diester is set out below.

Example 3: p-Methyl p-(4-hydroxybutoxy)benzoate

A solution containing 3990 g (15.0 M) of methyl p-(4-acetoxybutoxy) benzoate, 80 g p-toluenesulfonic acid (0.42 M) and 12 l. absolute methanol was stirred while refluxing in a 22 l. three-necked flask for four hours. Six liters of methanol were distilled off at atmospheric pressure and the remainder of solvent at reduced pressure. The residue was dissolved in 12 l. toluene and the solution was washed twice in portions with one-half volumes of water (this usually led to a pH of 4 for the second water wash). The washed toluene solution was dried over anhydrous sodium sulfate. After removal of the drying agent by filtration, the filtrate was cooled overnight to yield a crude crystalline product. This was filtered off and washed with petroleum ether or hexane and air dried. The yield of this first crop was 2047 g, m.p. 48°–52° C. A second crop of 525 g (m.p. 46°–48° C.) was obtained by condensing the toluene filtrate to one-half volume and repeating the procedure used in the isolation of the first crop. The combined yield was 2572 g (76.5%).

By this method the overall yield based on methyl p-hydroxybenzoate was 73.2%.

The preparation of methyl p-(ω-hydroxyalkoxy) benzoate according to the present invention has several advantages over the method disclosed in U.S. Ser. No. 253,418, including a greater initial and/or greater overall yield (73.2% reported as compared with about 35% using the method disclosed in U.S. Ser. No. 253,418). The diester intermediate is a novel composition and can be purified more readily by recrystallization than p-(4-hydroxybutoxy) benzoic acid for it has optimum solubility in a greater number of organic solvents. Use of the diester intermediate provides economy by reducing the amount of waste organic and inorganic by-products. In addition, the diester intermediate is easily purified and yields a high purity monomer of methyl p-(ω-hydroxyalkoxy) benzoate.

The diesters may also self-condense to a homopolymer according to the following reaction scheme:

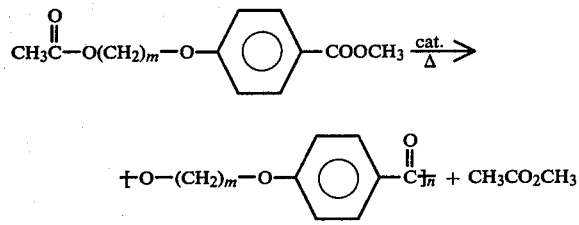

where the catalyst is an organo-metallic and/or inorganic catalyst containing one or more of the following transition elements: Sn, Sb, Pb, Ti. Heat is required in an amount sufficient for the formation of the homopolymer without destroying the starting materials or product. The reaction must be carried out in an inert atmosphere. The following examples illustrate methods for producing the C-2 and C-4 homopolymers.

Example 4: Formation of poly(ethoxybenzoate) (PEB)

Under a dry nitrogen atmosphere, the following materials were placed into a flame and vacuum dried 10 ml round-bottom flask, equipped with a short distilling head fitted with a receiver and a gas inlet nozzle:

| | |
|---|---|
| 1.0 g methyl p-(2-acetoxyethoxy) benzoate | (0.0042 mol) |
| 0.004 g dibutyltin oxide | |

The entire charge-containing assembly was removed from the nitrogen atmosphere and exposed to a high (less than 1 mm) vacuum for several hours. The charged reaction vessel was vented with nitrogen, and then heated to 100° C. After thorough mixing for 15 minutes at this temperature, the reaction mixture was subjected to the following heating scheme: 200° C. for 3.0 hours, 230° C. for 5.25 hours, and 250° C. for 1.25 hours. As the distillation of volatile byproducts slowed after 1.25 hours at 250° C., the receiver containing the distillate was replaced with an empty receiver. Then gradually over the course of 0.75 hours the pressure in the reaction flask was reduced to 0.05 mm. Under reduced pressure the reaction mixture was heated at 250° C. for 2.75 hours. At the end of this heating cycle, the reaction vessel was removed from the oil bath, equilibrated with nitrogen, and then allowed to cool to room temperature. The polymer was isolated after chilling in liquid nitrogen and then ground and dried.

Example 5: Formation of poly(p-n-butoxybenzoate) (PBB)

Under a dry nitrogen atmosphere, the following materials were placed into a flame and vacuum dried 100 ml two-neck, round-bottom flask, equipped with a paddle stirrer, a short distilling head fitted with a receiver and a gas inlet nozzle:

| | |
|---|---|
| 34.6 g methyl para(4-acetoxybutoxy) benzoate | (0.1301 mol) |
| 0.1 g dibutyltin oxide | |

After stoppering the open neck of the flask, the entire charge-containing assembly was removed from the nitrogen atmosphere and exposed to a high (less than 1 mm) vacuum for several hours. The charged reaction vessel was then vented with nitrogen, and heated to 100° C. Once the charge was liquified, the reaction flask was connected to an efficient mechanical stirrer and thorough mixing at 100° C. was performed for 15 minutes. Still under a continuous flow of nitrogen, the melted reaction mixture was then subjected to the following heating sequence: 200° C. for 2.5 hours, 230° C. for 2.5 hours, and 250° C. for 1.5 hours. As the distillation of the volatile by-products slowed after 1.5 hours at 250° C., the receiver containing the distillate was replaced with an empty receiver. Then gradually over the course of 0.75 hours the pressure in the reaction flask was reduced to 0.05 mm. Under reduced pressure the reaction mixture was heated at 250° C. for 6.0 hours. At the end of this heating cycle, the reaction vessel was removed from the oil bath, equilibrated with nitrogen, and then allowed to cool to room temperature. The polymer was isolated after chilling in liquid nitrogen and then ground and dried for 8 hours at 80° C. high vacuum.

The resulting polymer is a good fiber former, as indicated by the value of inherent viscosity set out in the appended chart.

The diesters may also be used to form copolyesters directly, without proceeding through the step of forming methyl p-(4-hydroxybutoxy) benzoate. The process comprises mixing the diester with another suitable ester in an inert atmosphere, and heating in the presence of an organometallic and/or inorganic catalyst containing one or more of the following transition elements: Sn, Sb, Pb, Ti, to form the copolyester. The amount of heat applied is suitable for formation of the copolyesters without destroying the reactants or product. Three examples of copolyester formations are set out below.

Example 6: Preparation of 76/24 PBB/$C_{18}$Succinate copolyester

Under a dry nitrogen atmosphere, the following materials were placed into a flame and vacuum dried 100 ml two-neck, round-bottom flask, equipped with a paddle stirrer, a short distilling head fitted with a receiver and a gas inlet nozzle:

| | |
|---|---|
| 26.3 g methyl para(4-acetoxybutoxy)benzoate | (0.0989 mol) |
| 4.7 g 2-octadecenyl succinic anhydride | (0.0133 mol) |
| 1.7 g 1,6-hexanediol | (0.0144 mol) |
| 0.1 g dibutyltin oxide | |

After stoppering the open neck of the flask, the entire charge-containing assembly was removed from the nitrogen atmosphere and exposed to a high (less than 1 mm) vacuum for several hours. The charged reaction vessel was then vented with nitrogen, and heated to 100° C. Once the charge was liquified, the reaction flask was connected to an efficient mechanical stirrer and thorough mixing at 100° C. was performed for 15 minutes. Still under a continuous flow of nitrogen, the melted reaction mixture was then subjected to the following heating sequence: 200° C. for 1.0 hours, 230° C. for 2.0 hours, and 250° C. for 8.25 hours. As the distillation of volatile by-products slowed after 8.25 hours at 250° C., the receiver containing the distillate was replaced with an empty receiver. Then gradually over the course of 0.75 hours the pressure in the reaction flask was reduced to 0.05 mm. Under reduced pressure the reaction mixture was heated at 250° C. for 7.3 hours. At the end of this heating cycle, the reaction vessel was removed from the oil bath, equilibrated with nitrogen, and then allowed to cool to room temperature. The polymer was isolated after chilling in liquid nitrogen and then ground and dried for 8 hours at 80° C. under vacuum. The fiber-forming characteristics of this copolymer are set out in the attached chart.

Example 7: Preparation of 78/22 PBB/$C_{18}$ Succinate

Under a dry nitrogen atmosphere, the following materials were placed into a flame and vacuum dried 100 ml two-neck, round-bottom flask equipped with a stainless steel paddle stirrer, a short distilling head fitting with a receiver, and a gas inlet nozzle:

| | |
|---|---|
| 32.4 g Methyl p-(4-acetoxybutoxy) benzoate | (0.1218 mol) |
| 5.1 g 2-octadecenyl succinic anhydride | (0.0144 mol) |
| 1.7 g 1,6-hexanediol | (0.0144 mol) |
| 0.03 g Butylstannoic acid | |

After stoppering the open neck of the flask, the entire charge-containing assembly was removed from the nitrogen atmosphere and exposed to a high (less than 1 mm) vacuum for several hours. The charged reaction vessel was then vented with nitrogen, and the reactants liquified by heating to 100° C. Once the charge was liquified, the reaction flask was connected to an efficient mechanical stirrer and thorough mixing at 100° C. was performed for 15 minutes. Still under a continuous flow of nitrogen, the melted reaction mixture was then subjected to the following heating sequence: 190° C. for 2.5 hours, 220° C. for 2.0 hours, and 240° C. for 2.0 hours. The reaction was then cooled to room temperature. Next a catalyst (0.48 ml), consisting of a mixture of tetrabutyl orthotitanate and magnesium acetate dissolved in a mixture of methanol and butanol, was quickly syringed into the reaction vessel via the side arm. Under a continuous flow of nitrogen, the reaction mixture was next heated according to the following scheme: 220° C. for 1.0 hours and 240° C. for 2.5 hours. As the distillation of volatile by-products slowed after 2.5 hours at 240° C., the receiver containing the distillate was replaced with an empty receiver. Then gradually over the course of 0.75 hours the pressure in the reaction flask was reduced to 0.05 mm. Under reduced pressure the reaction mixture was subjected to the following heating scheme: 240° C. for 3.0 hours and 255° C. for 5.5 hours. At the end of this heating cycle, the reaction vessel was removed from the oil bath, equilibrated with nitrogen, and then allowed to cool to room temperature. The polymer was isolated after chilling in liquid nitrogen and then ground and dried for 8 hours at 80° C. under vacuum.

Example 8: Preparation of 78/22 PBB/$C_{18}$ Succinate

Under a dry nitrogen atmosphere, the following materials were placed into a flame and vacuum dried 100 ml two-neck, round-bottom flask equipped with a stainless steel paddle stirrer, a short distilling head fitting with a receiver, and a gas inlet nozzle:

| | |
|---|---|
| 32.4 g Methyl para-(4-acetoxybutoxy) benzoate | (0.1218 mol) |
| 5.1 g 2-octadecenyl succinic anhydride | (0.0144 mol) |
| 1.7 g 1,6-hexanediol | (0.0144 mol) |

After stoppering the open neck of the flask, the entire charge-containing assembly was removed from the nitrogen atmosphere and exposed to a high (less than 1 mm) vacuum for several hours. The charged reaction vessel was then vented with nitrogen, and the reactants were melted by heating to 100° C. Once the charge was liquified, the reaction flask was connected to an efficient mechanical stirrer and thorough mixing at 100° C. was performed for 15 minutes. Next, the catalyst (0.56 ml), consisting of a mixture of tetrabutyl orthotitanate (0.1370 g.) and magnesium acetate (0.0056 g.) dissolved in a mixture of methanol and butanol, was quickly syringed into the reaction vessel via the side arm. Still under a continuous flow of nitrogen, the melted reaction mixture was then subjected to the following heating sequence: 190° C. for 2.5 hours, 220° C. for 2.0 hours, 240° C. for 4.0 hours, and 250° C. for 7.0 hours. As the distillation of volatile by-products slowed after 7.0 hours at 250° C., the receiver containing the distillate was replaced with an empty receiver. Then, gradually over the course of 0.75 hours the pressure in the reaction flask was reduced to 0.05 mm. Under reduced pressure the reaction mixture was subjected to the following heating scheme: 240° C. for 2.5 hours, 250° C. for 2.5 hours, and 260° C. for 2.0 hours. At the end of this heating cycle, the reaction vessel was removed from the oil bath, equilibrated with nitrogen, and then allowed to cool to room temperature. The polymer was isolated after chilling in liquid nitrogen and then ground and dried for 8 hours at 80° C. under vacuum.

It will be understood by those skilled in the art that variations and modifications of the specific embodiments described above may be employed without departing from the spirit and scope of the invention as defined in the appended claims.

under substantially anhydrous conditions to yield methyl p-(4-acetoxy-n-butoxy) benzoate.

2. A process as in claim 1 wherein said base is potassium carbonate with or without potassium iodide.

3. The process for producing methyl p-(4-hydroxy-n-butoxy) benzoate comprising reacting methyl p-(4-acetoxy-n-butoxy) benzoate with methanol in the presence of an acid to yield methyl p-(4-hydroxy-n-butoxy) benzoate.

4. The process of claim 1 wherein the acid is sulfuric acid or p-toluene sulfonic acid or sulfonated polystyrene.

5. The compound methyl p-(4-acetoxy-n-butoxy)benzoate.

| | | Extrusion Conditions | | Draw Conditions | | | Knot | Str. | | Young's Modulus |
|---|---|---|---|---|---|---|---|---|---|---|
| | $\eta_{inh}$ (@ 25° C. in HFIP) | $T^*_M$ | °C. | $\eta_{app}$ (poise) | Ratio/Temp (°C.) | | Dia. (mil) | $\times 10^{-3}$ (psi) | $\times 10^{-3}$ (psi) | Elong. (%) | $\times 10^{-3}$ (psi) |
| Description | | | | | 1st stage | 2nd stage | | | | | |
| PBB (Example #5) | 0.63 | 176–179 | 195 | 3472 | 4/56 | 1.375/75 | 9.4 | 43.2 | 60.5 | 20 | 632.6 |
| 76/24 PBB/ $C_{18}$ Succinate (Example #6) | 0.60 | 132–142 | 160 | 3975 | 4/63 | 1.5/78 | 7.7 | 31.1 | 45.1 | 41 | 52.1 |
| PEB (Example #4) | 0.21 | 209–213 | | | | | | | | | |

*by microscopy

We claim:

1. A process for producing methyl p-(4-acetoxy-n-butoxy) benzoate comprising reacting methyl p-hydroxybenzoate with an $\alpha,\omega$ acetoxy bromo- or chloro-n-butane, in the presence of a base and an organic solvent,